United States Patent [19]

Furrer et al.

[11] Patent Number: 4,713,455

[45] Date of Patent: Dec. 15, 1987

[54] CYCLIC DERIVATIVES OF ALKYL DIHYDROXYALKYLXANTHENES

[75] Inventors: Harald Furrer, Kelkheim; Hiristo Anagnostopulos, Taunusstein; Ulrich Gebert, Kelkheim, all of Fed. Rep. of Germany

[73] Assignee: Hoechst Aktiengesellschaft, Fed. Rep. of Germany

[21] Appl. No.: 848,139

[22] Filed: Apr. 4, 1986

Related U.S. Application Data

[62] Division of Ser. No. 420,932, Sep. 17, 1982, Pat. No. 4,616,020.

[30] Foreign Application Priority Data

Sep. 26, 1981 [DE] Fed. Rep. of Germany ....... 3138397

[51] Int. Cl.[4] ............................................ C07D 405/06
[52] U.S. Cl. .................................... 544/267; 544/273; 549/455; 549/563
[58] Field of Search ......................................... 544/267

[56] References Cited

U.S. PATENT DOCUMENTS 4,397,779 8/1983 Groman et al. ...................... 544/268
4,451,449 5/1984 Goring ................................ 544/268

OTHER PUBLICATIONS

Avico, et al., "Chemical Abstracts", vol. 57, 1962, col. 16605a.

Franzone, et al., "Chemical Abstracts", vol. 96, 1982, col. 96:6482n.

Primary Examiner—Glennon H. Hollrah
Assistant Examiner—James H. Turnipseed
Attorney, Agent, or Firm—Berman, Aisenberg & Platt

[57] ABSTRACT

Compounds of the formula

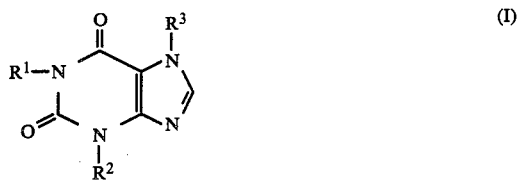

wherein one of the radicals $R^1$, $R^2$ or $R^3$ denotes a straight-chain alkyl group having 4 to 8 C atoms and two vicinal hydroxyl groups in the $\omega,\omega-1$ or $\omega-1,\omega-2$ positions and the two other radicals represent straight-chain or branched alkyl groups having up to 12 C atoms in the position of $R^1$ and $R^3$ and up to 4 C atoms in the position of $R^2$, the total of C atoms in these two alkyl substituents being a maximum of 14, are prepared by oxidation of the corresponding alkenylxanthines and by alkylation with compounds which introduce the dihydroxyalkyl radical or a precursor thereof. The dihydroxyalkyldialkylxanthines are suitable for the treatment of obstructive respiratory tract diseases.

11 Claims, No Drawings

CYCLIC DERIVATIVES OF ALKYL DIHYDROXYALKYLXANTHENES

This application is a division of Application Ser. No. 420,932, filed Sept. 17, 1982 now U.S. Pat. No. 4,616,020.

The invention relates to new medicaments which are suitable, in particular, for the treatment of obstructive diseases of the respiratory tract, the pharmacologically active vicinal dihydroxyalkylxanthines contained in them, processes for the preparation of these xanthine derivatives and intermediate products for this purpose.

The xanthine compounds, which act as phosphodiesterase inhibitors, have a pre-eminent position among the bronchospasmolytic agents hitherto known (cf. B. Hellwig, Moderne Arzneimittel (Modern Drugs), Stuttgart 1980, page 1,274), since they have no $\beta_2$-sympathomimetic activity and are thus particularly suitable for the long-term therapy which is always necessary for chronic obstructive disorders of the respiratory tract. Of this group of substances, the naturally occurring xanthine derivative theophylline (1,3-dimethylxanthine), has been the undisputed agent of choice in asthma therapy for several decades now. Its activity, which is clinically well established, is, however, contrasted by the disadvantages of its very narrow therapeutic range, its serious gastrointestinal, cardiovascular and renal side-effects, as well as those in the central nervous system, and the fact that it can only be used enterally due to its lack of water solubility, and these disadvantages are the basis for the desire of clinicians for, and the pharmaceutical research directed at finding, products having a greater therapeutic safety.

It has in fact been possible, by the preparation of water-soluble salts or addition compounds, such as, for example, theophylline-ethylenediamine (aminophylline), to obtain formulations of theophylline which can also be administered parenterally, but these are not associated with a significant increase in the therapeutic range or a decrease in the abovementioned undesired side-effects; especially since the ethylenediamine itself, which functions as a solubilizer in aminophylline, exerts a deleterious effect on the cardiovascular system.

Thus, there have been many attempts to obtain, by variations in the structure of the theophylline molecule, better tolerated compounds having, if possible, a greater bronchospasmolytic activity.

The only synthetic theophylline derivative which has found a certain therapeutic use is diphylline[7-(2,3-dihydroxypropyl)-1,3-dimethylxanthine]. The 2,3-dihydroxypropyl group in the 7-position does confer a good water solubility on this product, so that the undesired use of solubilizers for parenteral administration is no longer necessary and the interfering theophylline-like side-effects are much less pronounced, but these advantages are, at the same time, paid for by a drastic decrease in the bronchospasmolytic activity compared to that of theophylline.

In systematic continuation of these investigations, the two methyl groups in the 1- and 3-positions have been exchanged for longer alkyl groups, while retaining the 2,3-dihydroxypropyl radical in the 7-position of the xanthine skeleton. This led to 7-(2,3-dihydroxypropyl)-1,3-dipropylxanthine, which is described in German Offenlegungsschrift No. 2,716,402 and which is a compound readily soluble in water, which is said almost to reach the bronchospasmolytic activity of theophylline and, at the same time, to have a lower acute toxicity and fewer disadvantageous side-effects. Nevertheless, this product has not hitherto found acceptance in asthma therapy. Furthermore, according to the abovementioned Offenlegungsschrift, it induces stimulation of the central nervous system, although this is markedly weaker than that of theophylline, which can lead to restlessness and sleep disturbances. Accordingly, water-soluble xanthine compounds, which are superior to theophylline in respect of strength of action and therapeutic range and which induce no significant side-effects, in particular no stimulation of the central nervous system, would still represent a genuine enrichment of the therapy of obstructive disorders of the respiratory tract.

It has now been found, surprisingly, that increasing the length of the dihydroxypropyl radical, which has not hitherto been investigated, irrespective of its position on the xanthine skeleton, leads to compounds which fulfil these strict therapeutic demands. It is true that two xanthine derivatives of this type, namely 1-(5,6-dihydroxyhexyl)-3,7-dimethylxanthine and 1-(4,5-dihydroxyhexyl)-3,7-dimethylxanthine in the threo and erythro forms, have already been described in the literature (Arzneimittelforschung (Drug Res.) 22, 1,144–1,151 (1972)), but these compounds were merely isolated and identified as metabolites of the vasotherapeutic agent pentoxifylline. Accordingly, there are no data on their pharmacological properties in this publication.

Thus, the present invention relates to medicaments which contain vicinal dihydroxyalkylxanthines of the general formula I

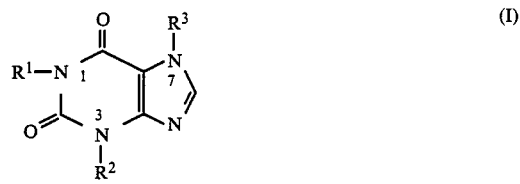

wherein one of the radicals $R^1$, $R^2$ or $R^3$ denotes a straight-chain alkyl group having 4 to 8 C atoms and two vicinal hydroxyl groups in the $\omega,\omega-1$ or $\omega-1,\omega-2$ positions and the two other radicals represent straight-chain or branched alkyl groups having up to 12 C atoms in the position of $R^1$ and $R^3$ and up to 4 C atoms in the position of $R^2$, the total of C atoms in these two alkyl substituents being a maximum of 14.

In this context, those medicaments are preferred which contain compounds of the formula I in which $R^1$ or $R^2$ represents an $(\omega,\omega-1)$-dihydroxyalkyl radical having 5 or 6 C atoms and the two alkyl substituents $R^2$ and $R^3$ or $R^1$ and $R^3$ together comprise 3 to 6 C atoms.

A further preferred embodiment of the invention relates to medicaments which contain those compounds of the formula I in which $R^3$ denotes an $(\omega,\omega-1)$-dihydroxyalkyl group having 4 to 7 C atoms or a 4,5-dihydroxyhexyl group, and the total of C atoms in the two alkyl radicals $R^1$ and $R^2$ is 3 to 7. Among these medicaments, those in turn are particularly preferred which contain those compounds of the formula I in which $R^3$ represents a 5,6-dihydroxyhexyl radical, such as, for example, in 3-ethyl-7-(5,6-dihydroxyhexyl)-1-propylxanthine.

A further particular embodiment of the invention comprises the compounds of the formula I not being administered per se, but in the form of a prodrug, from which the dihydroxyalkylxanthines, having bronchospasmolytic activity, with their substituents $R^1$, $R^2$ and $R^3$ defined in the foregoing, can only be liberated by biotransformation in the organism. For this purpose, for example, the epoxides having the structural element of the formula IV and, in particular, the cyclic acetals having the structural element of the formula IX, when these are completely alkylated, which are dealt with below as intermediate products in the preparation process, are suitable.

The invention also relates to new vicinal dihydroxyalkylxanthines of the formula I, in which one of the radicals $R^1$, $R^2$ or $R^3$ denotes a straight-chain alkyl group having 4 to 8 C atoms and two vicinal hydroxyl groups in $\omega,\omega-1$ or $\omega-1,\omega-2$ positions and the two other radicals represent straight-chain or branched alkyl groups having up to 12 C atoms in the position of $R^1$ and $R^3$ and up to 4 C atoms in the position of $R^2$, the total of C atoms in these two alkyl substituents being, however, a maximum of 14 and $R^2$ and $R^3$ not both being methyl, when $R^1$ represents a 4,5- or 5,6-dihydroxyhexyl radical.

In this context, particularly suitable compounds are those in which $R^1$ or $R^2$ represents an $(\omega,\omega-1)$-dihydroxyalkyl radical having 5 or 6 C atoms and the two alkyl substituents $R^2$ and $R^3$ or $R^1$ and $R^3$ together contain 3 to 6 C atoms, and also those wherein $R^3$ denotes an $(\omega,\omega-1)$-dihydroxyalkyl group having 4 to 7 C atoms or a 4,5-dihydroxyhexyl group, and the two alkyl radicals $R^1$ and $R^2$ together contain 3 to 7 C atoms. of the last-mentioned group of compounds, the 7-(5,6-dihydroxyhexyl)-1,3-dialkylxanthines having a total of 3 to 7 C atoms in the two alkyl radicals $R^1$ and $R^2$, such as, for example, 3-ethyl-7-(5,6-dihydroxyhexyl)-1-propylxanthine, in turn represent particularly preferred compounds according to formula I.

The invention further relates to processes for the preparation of the vicinal dihydroxyalkylxanthines according to formula I.

An example of a process comprises starting with xanthines of the formula II

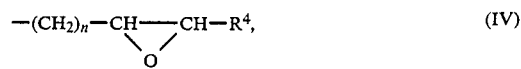

in which one of the radicals $R^{1'}$, $R^{2'}$ or $R^{3'}$ is an $(\omega-1)$- or $(\omega-2)$-alkenyl group of the formula III $$-(CH_2)_n-CH=CH-R^4 \qquad (III),$$

having 4 to 8 C atoms, $R^4$ denoting hydrogen or methyl, and the other two substituents represent hydrogen or alkyl as defined in the formula I with regard to $R^1$ to $R^3$. and (a) reacting them on the olefinic double bond with suitable oxidizing agents to give new epoxyalkylxanthines having the structural element of the formula IV

and hydrolytically opening their oxirane ring with formation of dihydroxyalkylxanthines having the structural unit of the formula V $$-(CH_2)_n-CH-CH-R^4 \qquad (V)$$
$$\phantom{-(CH_2)_n-}\overset{|}{OH}\ \overset{|}{OH}$$

or (b) dihydroxylating on the olefinic double bond with customary oxidizing agents to give directly the dihydroxyalkylxanthines having the structural element characterized by formula V, and then alkylating those diols obtained according to (a) or (b), which still carry hydrogen in the positions of $R^{1'}$, $R^{2'}$ and/or $R^{3'}$, optionally in the presence of basic agents or in the form of their salts, with alkylating agents of the formula VI $$R^5-X \qquad (VI),$$

in which X denotes halogen, preferably chlorine or bromine, or a sulfonate or phosphate grouping and $R^5$ denotes the alkyl radicals defined for formula I, to give the compounds of the formula I.

The alkenyl-, monoalkyl- and dialkyl-alkenyl-xanthines of the formula II used as starting materials in this process are known, inter alia, from German Offenlegungsschriften Nos. 2,714,953 and 2,836,147.

Examples of suitable oxidizing agents for the epoxidation of the olefinic side-chain according to formula III are chromium(VI) oxide, preferably in acetic anhydride and carbon disulfide or carbon tetrachloride; or compounds containing peroxide groups, such as potassium peroxomonosulfate in the presence of ketones, preferably acetone, in a homogeneous phase or in a two-phase system with phase-transfer catalysis; peroxyboranes, which are advantageously produced in situ from boric acid or its derivatives and hydroperoxides; triphenylsilyl hydroperoxide; hydrogen peroxide in the presence of coreactants, such as, for example, aliphatic or aromatic carbonitriles (for example acetonitrile or benzonitrile), optionally substituted cyanamide or isocyanates (for example phenyl isocyanate); hydrogen peroxide or alkyl or aralkyl hydroperoxides, such as, for example, tert.-butyl hydroperoxide, 1-phenylethyl hydroperoxide and cumene hydroperoxide, in the presence of either basic agents or, preferably, particular catalysts, such as, for example, tungstic acid, vanadium(V) oxide, molybdenum hexacarbonyl and vanadium or molybdenum acetylacetonates; and, in particular, percarboxylic acids, such as, for example, performic, peracetic, trifluoroperacetic, monopermaleic, monopersuccinic, perbenzoic, 4-nitroperbenzoic and, preferably, 3-chloroperbenzoic and monoperphthalic acid.

Epoxidation with the aid of percarboxylic acids (Prileschajew reaction) is advantageously carried out in a solvent or distributing agent which is inert towards the reactants and which has been found to exert a considerable effect on the rate of reaction. Since solvents which can form hydrogen bonds with the percarboxylic acids generally decrease the rate of reaction, aromatic hydrocarbons, such as benzene or toluene, and halogenated hydrocarbons, such as dichloromethane, chloroform or carbon tetrachloride, are frequently preferred to ethers, such as diethyl ether, dioxane, tetrahydrofuran or ethylene glycol dimethyl ether, alcohols, esters and carboxylic acids. The reaction is customarily carried out at temperatures between −10° and +40° C., preferably at room temperature, the reaction time varying from a few minutes up to several hours.

The percarboxylic acids are usually employed for the reaction in an isolated form, but they can also be produced in situ in the reaction mixture from, for example, the corresponding carboxylic acid and hydrogen peroxide.

On using peracids of strong carboxylic acids, such as, for example, trifluoroperacetic acid, it is advisable to decrease the acid concentration by working in a heterogeneous system or by the addition of buffer substances, such as sodium carbonate, sodium bicarbonate or disodium hydrogen phosphate, in order to suppress undesired secondary reactions of the carboxylic acid, which is produced in the reaction, with the initially formed epoxide.

The epoxyalkylxanthines according to formula II having the structural unit of the formula IV can, however, also be obtained by base-catalyzed dehydrohalogenation of corresponding halogenohydrins, which in turn can be obtained, for example, by adding hypohalous acids, such as, for example, hypochlorous acids, to the olefinic double bond of the alkenylxanthines according to formulae II and III. The reaction of these olefins with N-halogenosuccinimides, such as N-bromosuccinimide, or chloramine T in water or mixtures of solvents containing water also leads to the halogenohydrins. The basic dehydrohalogenating agents usually used are alkali metal or alkaline earth metal hydroxides or carbonates, preferably sodium, potassium or calcium hydroxide or sodium or potassium carbonate, but organic bases or other oxiranes, such as ethylene oxide or 1,2-epoxypropane, can also be employed successfully.

The epoxyalkylxanthines can either be isolated in the pure form or further processed as crude products.

The hydrolytic cleavage of the epoxyalkylxanthines to give the vicinal diols having the structural element of the formula V is carried out in an aqueous medium, to which, if necessary to increase the solubility, an organic solvent which is miscible with water is added, for example tetrahydrofuran, dioxane or ethylene glycol dimethyl ether, advantageously in the presence of acid catalysts, preferably weakly nucleophilic acids, such as sulfuric, perchloric or p-toluenesulfonic acid, or strongly acid cation exchanger resins (for example Nafion-H ™), at temperatures between 20° and 100° C., but preferably at room temperature, by stirring for several hours. However, in principle, the oxirane ring opening is also possible under neutral or alkaline conditions.

Customary oxidizing agents for the direct vicinal dihydroxylation of the alkenylxanthines according to formulae II and III to give the dihydroxyalkylxanthines characterized by the structural unit of formula V, are represented by, for example, hydrogen peroxide in the presence of formic acid or glacial acetic acid, chromyl chloride, potassium permanganate, triphenylmethylphosphonium permanganate, iodine in the presence of silver carboxylates or thallium(I) carboxylates, such as, for example, thallium(I) acetate, selenium dioxide, molybdenum(VI) oxide and, in particular, osmium tetroxide.

When using osmium tetroxide as the oxidizing agent, the reagent can either be employed in the stoichiometric amount or in catalytic amounts with the addition of a secondary oxidizing agent, which regenerates the osmium tetroxide from the initially produced cyclic esters, with oxidative hydrolysis to give the diols.

In the non-catalytic dihydroxylation of the olefinic double bond with stoichiometric amounts of osmium tetroxide, the process is advantageously carried out in solvents not having a reducing action, preferably ethers, such as diethyl ether, tetrahydrofuran and dioxane, or hydrocarbons, such as benzene, cyclopentane or cyclohexane, optionally with the addition of a tertiary amine, such as, in particular, pyridine or quinoline, isoquinoline, 3- or 4-picoline, at temperatures between 0° C. and the boiling point of the particular solvent, preferably at room temperature, it being possible for the reaction times to be from a few minutes to several hours. Then the osmium(VI) ester complexes, which are produced as intermediates in this process, are advantageously reductively hydrolyzed, the use of sodium or potassium sulfite or bisulfite, hydrogen sulfide, lithium aluminum hydride or catechol or alkaline mannitol solution in aqueous or aqueous-alcoholic medium having been found particularly useful. However, oxidative hydrolysis of the complexes is also possible; but it is advisable, in this case, to carry out the dihydroxylation at the outset with catalytic amounts of osmium tetroxide in the presence of secondary oxidizing agents, such as, for example, hydrogen peroxide, metal chlorates (for example sodium or potassium and, in particular, silver or barium chlorate), sodium perchlorate, oxygen, sodium periodate or hypochlorite and, in particular, tert.-butyl hydroperoxide or trialkylamine N-oxides (for example N-methylmorpholine N-oxide, trimethylamine N-oxide or triethylamine N-oxide).

The alkylation of the dihydroxyalkylxanthines with the compounds of the formula VI is usually carried out in a distributing agent or solvent which is inert towards the reactants. Dipolar aprotic solvents, for example formamide, dimethylformamide, dimethylacetamide, N-methylpyrrolidone, tetramethylurea, hexamethylphosphoric triamide, dimethyl sulfoxide, acetone or butanone are particularly suitable; however, alcohols, such as methanol, ethylene glycol and its ethers, ethanol, propanol, isopropanol and the various butanols; hydrocarbons, such as benzene, toluene or xylenes; halogenated hydrocarbons, such as dichloromethane or chloroform; pyridine and mixtures of the solvents mentioned or their mixtures with water can also find use.

The reactions are advantageously carried out in the presence of a basic condensing agent. Examples of suitable agents for this purpose are alkali metal or alkaline earth metal hydroxides, carbonates, hydrides, alcoholates or organic bases, such a trialkylamines (for example triethylamine or tributylamine), quaternary ammonium or phosphonium hydroxides and crosslinked resins having fixed ammonium or phosphonium groups, which are optionally substituted.

However, the xanthine derivatives can also be employed directly in the alkylation reaction in the form of their salts prepared separately, such as the alkali metal, alkaline earth metal or optionally substituted ammonium or phosphonium salts. Furthermore, the dihydroxyalkylxanthines and their monoalkylated derivatives can be readily alkylated both in the presence of the abovementioned inorganic condensing agents and also in the form of their alkali metal or alkaline earth metal salts, with the assistance of so-called phase-transfer catalysts, for example tertiary amines, quaternary ammonium or phosphonium salts or crown ethers, preferably in a two-phase system under the conditions of phase-transfer catalysis.

In the introduction of the alkyl radicals by the procedures described in the foregoing, the reaction is generally carried out at a temperature between 0° C. and the boiling point of the reaction medium used in each case, preferably between 20° and 130° C., if appropriate under elevated or reduced pressure, but usually under atmospheric pressure, it being possible for the reaction time to be from less than one hour to several hours.

In this process for those dihydroxyalkylxanthines, into which two alkyl radicals are still to be introduced, either identical or different substituents can be attached consecutively or two similar alkyl groups can be attached with the xanthine skeleton without isolation of intermediate products in a one-pot reaction.

A further process for the preparation of compounds of the formula I, which is likewise preferred, comprises reacting xanthines of the formula VII

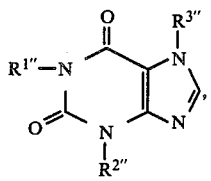
(VII)

in which a maximum of two of the substituents $R^{1''}$ to $R^{3''}$ represent alkyl defined for formula I with regard to $R^1$ to $R^3$ and a maximum of two of these radicals denote hydrogen, optionally in the presence of basic agents or in the form of their salts (a) with alkylating agents of the formula VIII

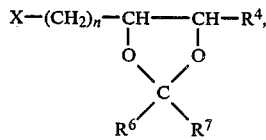
(VIII)

in which the alkyl chain has a total of 4 to 8 C atoms and $R^4$ denotes hydrogen or methyl, $R^6$ and $R^7$, independently of one another, denote hydrogen, lower alkyl preferably having up to 4 C atoms, phenylalkyl having up to 2 C atoms in the alkyl moiety or optionally substituted phenyl and X denotes halogen, preferably chlorine or bromine, or a sulfonate or phosphate grouping, to give new dialkylated or trialkylated xanthines having the structural element of the formula IX

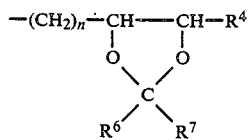
(IX)

and opening their 1,3-dioxolane ring hydrolytically, splitting off $R^6\text{-CO-}R^7$ and forming dihydroxyalkylxanthines having the structural unit of the formula V

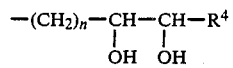
(V)

or (b) with alkylating agents of the formula X

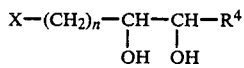
(X)

in which the alkyl chain has a total of 4 to 8 C atoms and $R^4$ and X have the meanings indicated for formula VIII, directly to give the dihydroxyalkylxanthines, having the structural element characterized by formula V, and then reacting the monoalkyldihydroxyalkylxanthines obtained according to (a) or (b), which still carry a hydrogen atom in the position of $R^{1''}$, $R^{2''}$ or $R^{3''}$, optionally in the presence of basic agents or in the form of their salts with alkylating agents of the formula VI $$R^5\text{—}X \qquad (VI)$$

in which X and $R^5$ have the meanings defined for formula VI in claim 12, to give the compounds of the formula I or initially alkylating the dialkylated xanthines prepared according to (a), having the structural element of the formula IX, with the compounds of the formula $R^5\text{-}X$ (VI) and then hydrolytically cleaving the dioxolane ring with formation of the dihydroxyalkylxanthines according to formula I.

The monalkylxanthines or dialkylxanthines of the formula VII and the alkylating agents of the formulae VIII and X used as starting materials in this process are largely known or can easily be prepared by methods known from the literature.

Thus, the compounds of the formula VIII, for example, can be obtained from the triols of the formula XI

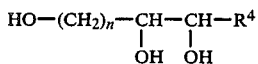
(XI)

by reaction of the two vicinal hydroxyl groups with aldehydes or ketones or with their acetals, with proton catalysis, and subsequent replacement of the isolated terminal hydroxyl function with halogen using inorganic acid halides, or its esterification with sulfonyl or phosphonyl halides or anhydrides, advantageously in the presence of basic agents, from which in turn the compounds of the formula X can be prepared by acid hydrolysis of the 1,3-dioxolane ring. The alkenyl halides of the formula XII $$\text{Hal—}(CH_2)_n\text{—CH=CH—}R^4 \qquad (XII)$$

can also serve as starting materials for the preparation of compounds of the formulae VIII and X, either by subjecting them, as described for the alkenylxanthines, to epoxidation on the olefinic double bond and then hydrolyzing the oxirane ring with acid or by oxidizing in a one-step reaction directly to the dihydroxyalkyl halides of the formula X and converting these, if appropriate, with aldehydes or ketones or their acetals into 1,3-dioxolanes of the formula VIII.

The reactions of the xanthine derivatives with the alkylating agents of the formulae VI, VIII and X are advantageously carried out under the reaction conditions already described in detail for the alkylation of the dihydroxyalkylxanthines and monoalkyldihydroxyalkylxanthines with the compounds of the formula VI. However, if the compounds of the formula X are used to introduce the dihydroxyalkyl radical, those having a total of either 6 to 8 C atoms, when $R^4$ has the meaning of hydrogen, or 7 to 8 C atoms, when $R^4$ denotes a methyl group, in the alkyl chain are preferred, since the diols of the formula X having shorter chains have a particular tendency to form tetrahydrofuran derivatives under the alkaline conditions of the alkylation reaction, which can lead to a noticeable reduction in the yields of desired alkylation product.

The hydrolytic cleavage of the 1,3-dioxolane ring in the xanthines of the formula VII having the structural element of the formula IX to give the dihydroxyalkylxanthines characterized by the structural unit of the formula V is normally carried out in an aqueous medium, optionally with the addition of a solubilizer, such as tetrahydrofuran, dioxane or ethylene glycol dimethyl ether, advantageously in the presence of acids, for example formic, oxalic, tartaric, citric, sulfuric, perchloric, phosphoric or p-toluenesulfonic acid, or an acid ion exchanger (for example Nafion-H), at temperatures between 20° C. and the boiling point of the reaction mixture, preferably 50° and 100° C., it being possible for the reaction time to be from several minutes to a few hours. Moist silica gel, having a water content up to 10%, is also a reagent which can be used for the deacetalization, the reaction preferably being carried out in optionally halogenated hydrocarbons, such as benzene, toluene, dichloromethane or chloroform, at room temperature.

A further method for preparing the xanthines of the formula VII with the structural element of the formula IX containing the dioxolane ring comprises adding carbonyl compounds of the formula $R^6$—CO—$R^7$ onto the oxirane ring of the epoxyalkylxanthines according to formula II, having the structural unit of the formula IV. This reaction is advantageously carried out in the presence of acid catalysts, preferably Lewis acids, such as boron trifluoride, zinc(II) chloride, tin(IV) chloride or copper(II) sulfate, at temperatures between 0° and 60° C. However, quaternary ammonium salts, for example tetraethylammonium halides, are also able to catalyze the addition reaction to give the cyclic acetals.

The vicinal dihydroxyalkylxanthines of the formula I have either one or two asymmetric C atoms, depending on the position of the two hydroxyl groups in the side chain according to formula V, and can thus be present in stereoisomeric forms. The invention thus relates both to the pure stereoisomeric compounds and also to their mixtures.

The medicaments according to the invention can be administered orally, rectally, parenterally or as an aerosol.

Examples of suitable solid or liquid galenic formulations are granules, powders, tablets, coated tablets, (micro)capsules, suppositories, syrups, emulsions, suspensions, aerosols, drops or injectable solutions as well as formulations with protracted release of the active compound, in the preparation of which galenic auxiliaries, such as vehicles, disintegrants, binders, coating agents, swelling agents, lubricants or emollients, flavoring materials, sweetening agents or solubilizers, are used. Examples of frequently used galenic auxiliaries which may be mentioned are lactose, mannitol and other sugars, talc, lactalbumin, gelatin, starch, cellulose and its derivatives, animal and vegetable oils, polyethylene glycols and solvents, such as, for example, sterile water.

The formulations are preferably produced and administered as dosage units, each unit containing a specified dose of active substance according to formula I. This dose can be up to 1,000 mg, but preferably 50 to 300 mg, for fixed dosage units, such as tablets, capsules and suppositories, and can be up to 200 mg, but preferably 20 to 100 mg, for injection solutions in vials.

For the treatment of an adult patient suffering from bronchial obstruction, daily doses of 100 to 500 mg of active compound, preferably 200 to 300 mg, on oral administration and of 20 to 150 mg, preferably 40 to 80 mg, on intravenous administration are indicated, depending on the effectiveness of the compounds according to formula I in humans. In certain circumstances, however, higher or lower daily doses can also be appropriate. The administration of the daily dose can be carried out either by a single administration in the form of a single dosage unit or of several smaller dosage units, or by several administrations of sub-divided doses at specified intervals.

Finally, in the preparation of the abovementioned galenic formulations, the xanthine derivatives of the formula I can also be formulated together with other suitable active compounds, for example antiallergic and antitussive agents, expectorants, sedatives, peripheral vasotherapeutic agents, antihistamines and also other bronchospasmolytic agents, such as $\beta_2$-sympathomimetic agents or parasympatholytics.

EXAMPLES

The structure of all the compounds described in the following text was confirmed by elementary analysis and IR and $^1$H NMR spectra.

EXAMPLE 1

3-Ethyl-7-(5,6-dihydroxyhexyl)-1-propylxanthine (a) 1-Hydroxy-5,6-isopropylidenedioxyhexane

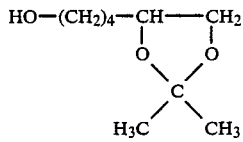

3 ml of 98% strength sulfuric acid were added dropwise in the course of 5 minutes to a mixture of 830 g of 1,2,6-hexanetriol (97% pure) and 828 ml of 2,2-dimethoxypropane (98% pure) at room temperature. After stirring for a further hour at 25° C., 30 g of potassium carbonate were added, the mixture was stirred another hour and then vacuum-distilled over a 10 cm packed column.

Yield:
897 g (86% of theory),
Boiling point (0.5 mbar) 83°–87° C.,
Refractive index $n_D° = 1.4452$.

(b) 1-Chloro-5,6-isopropylidenedioxyhexane

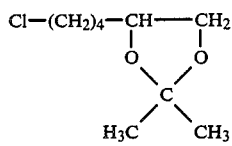

77 ml of thionyl chloride were added dropwise with stirring in the course of 3 hours to a solution of 176.4 g of 1-hydroxy-5,6-isopropylidenedioxyhexane and 155 ml of triethylamine in 1,300 ml of toluene at 5°–7° C. internal temperature. After stirring at 20°–25° C. for a further half an hour, the mixture was heated at 70° C. until evolution of SO₂ was complete (about 4 hours). The mixture was then cooled down and the precipitate which separated out was filtered off with suction. After washing with 100 ml of toluene, the toluene phases were combined, washed to neutrality, dried and evaporated under reduced pressure. 15 g of potassium carbonate were added to the residue and this was distilled in vacuo over a packed column.

Yield:
149.6 g (77.6% of theory),
Boiling point (0.15 mbar) 48°–50° C.,
Refractive index $n_D^{18} = 1.4482$.

(c) 3-Ethyl-7-(5,6-isopropylidenedioxyhexyl)xanthine

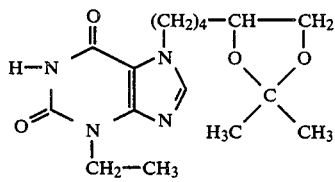

A mixture of 360.4 g of 3-ethylxanthine, 409.2 g of 1-chloro-5,6-isopropylidenedioxyhexane and 284.7 g of potassium carbonate in 3 l of dimethylformamide was heated at 100° C. with stirring for 2 hours. After evaporation of the suspension under reduced pressure, the residue was taken up with 1.1 l of 2N sodium hydroxide solution and thoroughly extracted with methylene chloride. The collected methylene chloride phases were washed again with 2N sodium hydroxide solution, then washed with water to neutrality, dried and evaporated under reduced pressure. 94.5 g of crude 3-ethyl-1,7-bis(5,6-isopropylidenedioxyhexyl)xanthine were obtained as a by-product. The combined aqueous phases, which were alkaline with sodium hydroxide, were treated dropwise with 33% strength sulfuric acid at room temperature, with stirring, until pH 10 was reached. The precipitate was filtered off with suction, washed to neutrality and dried at 100° C. in vacuo.

Yield:
508 g (75.5% of theory);
Melting point: 123°–124° C.;
$C_{16}H_{24}N_4O_4$ (MW=336.4).
Analysis: calculated: C 57.13%; H 7.19%; N 16.66%; found: C 56.92%; H 7.21%; N 16.68%.

(d) 3-Ethyl-7-(5,6-dihydroxyhexyl)-1-propylxanthine

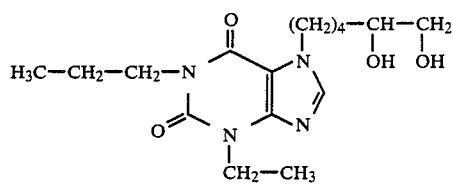

336.4 g of 3-ethyl-7-(5,6-isopropylidenedioxyhexyl)xanthine, 151 g of 1-bromopropane and 138 g of potassium carbonate in 1.5 l of dimethylformamide were stirred for 48 hours at an internal temperature of 70° C. After removal of the solvent under reduced pressure, the residue was taken up with methylene chloride, washed with dilute sodium hydroxide solution and the neutralized and dried methylene chloride phase was evaporated. The residue was heated in 1 l of sulfuric acid, at a pH of 0.5, for 2 hours at 100° C. After cooling down, the mixture was neutralized, evaporated under reduced pressure and the residue was taken up with methylene chloride. The methylene chloride phase was washed with dilute sodium hydroxide solution and with water, dried and evaporated under reduced pressure.

The crude product was recrystallized from methylene chloride/diethyl ether.

Yield:
259 g (76.5% of theory),
Melting point: 96°–98° C.,
$C_{16}H_{26}N_4O_4$ (MW=338.4).
Analysis: calculated: C 56.79%; H 7.74%; N 16.56%; found: C 56.86%; H 7.56%; N 16.60%.

EXAMPLE 2

1,3-Diethyl-7-(5,6-dihydroxyhexyl)xanthine

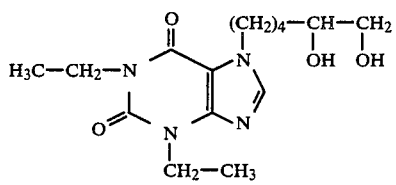

This compound was obtained by each of the following procedures (A) to (C).

(A) A mixture of 62.5 g of 1,3-diethylxanthine, 62.7 g of 1-chloro-5,6-isopropylidenedioxyhexane, 42.7 g of potassium carbonate and 450 ml of dimethylformamide was stirred at 120° C. for 10 hours. After evaporation under reduced pressure, the residue was taken up with 300 ml of 1N sodium hydroxide solution and extracted with methylene chloride. The methylene chloride phase was washed with dilute sodium hydroxide solution, washed to neutrality, dried and evaporated under reduced pressure. The crude product was distilled under 0.027 mbar and at a bath temperature of 130°–150° C. in a thin-layer evaporator, and 107.2 g were obtained:

1,3-Diethyl-7-(5,6-isopropylidenedioxyhexyl)xanthine

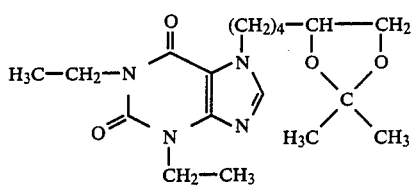

The latter was taken up in 1.4 l of methanol and 350 ml of water and, after the addition of 1.5 ml of perchloric acid (70% strength), was stirred at 70° C. for 1 hour. After cooling down to room temperature, the mixture was neutralized with sodium bicarbonate solution and evaporation to dryness under reduced pressure. The residue was extracted with 1.5 l of methylene chloride and the extract was evaporated. 92.5 g (95% of theory) of crude product were obtained, which, after recrystallization twice from methylene chloride/diethyl ether (volume ratio 2:3), gave 1,3-diethyl-7-(5,6-dihydroxyhexyl)xanthine, which was pure by thin-layer chromatography.

Yield:
81.7 g (83.9% of theory),
Melting point: 94°–95° C.,
$C_{15}H_{24}N_4O_4$ (MW=324.4).
Analysis: calculated: C 55.54%; H 7.46%; N 17.27%; found: C 55.52%; H 7.52%; N 17.02%.

(B) The above product was also obtained by hydrolysis of 1,3-diethyl-7-(5,6-epoxyhexyl)xanthine (melting point: 58°–59° C.).

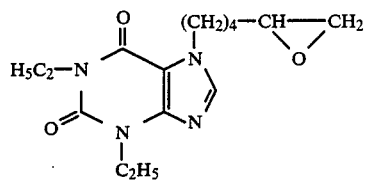

in analogy to Example 3.

(C) The same compound was also obtained by hydroxylation of 1,3-diethyl-7-(5-hexenyl)xanthine

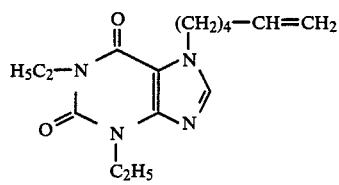

with osmium tetroxide: 0.73 g of 1,3-diethyl-7-(5-hexenyl)xanthine in 11 ml of diethyl ether was added dropwise with stirring in 5 minutes to 0.65 g of osmium tetroxide in 11 ml of diethyl ether at room temperature.

After standing overnight, the precipitate (1.2 g) was filtered off with suction. This was stirred under reflux in a mixture of 55 ml of water, 15 ml of ethanol and 11.2 g of sodium sulfite heptahydrate for 3 hours. After cooling down, the precipitate formed was separated off and the filtrate was extracted with methylene chloride. After drying and evaporating the collected methylene chloride phases under reduced pressure, 0.6 g of crude product was obtained, which gave 1,3-diethyl-7-(5,6-dihydroxyhexyl)xanthine as the monohydrate after recrystallization from diethyl ether.

Yield:
0.47 g (57.7% of theory),
Melting point: 77°–78° C. (monohydrate)
$C_{15}H_{24}N_4O_4.H_2O$ (MW=342.4).
Analysis: calculated: C 52.62%; H 7.65%; N 16.36%; found: C 52.48%; H 7.69%; N 16.20%.

EXAMPLE 3

1,3-Dimethyl-7-(5,6-dihydroxyhexyl)xanthine (a) 1,3-Dimethyl-7-(5,6-epoxyhexyl)xanthine

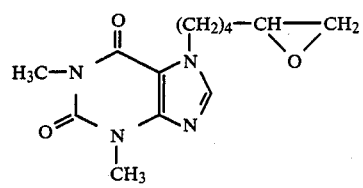

A solution of 31 g of 1,3-dimethyl-7-(5-hexenyl)xanthine and 34.9 g of m-chloroperbenzoic acid (70% pure) in 700 ml of chloroform was stirred at room temperature for 48 hours. The mixture was shaken with 10% strength sodium dithionite solution until the test with starch-iodide paper was negative, and washed with sodium bicarbonate solution and then with water to neutrality, dried and evaporated under reduced pressure.

Purification of the crude product was by means of column chromatography on silica gel (mobile phase: methylene chloride/acetone, volume ratio 7/3) and by recrystallization from petroleum ether.

Yield:
20.8 g (63.2% of theory), melting point, 59°–60° C.,
$C_{13}H_{18}N_4O_3$ (MW=278.3).
Analysis: calculated: C 56.10%; H 6.52%; N 20.13%; found: C 55.87%; H 6.51%; N 19.91%.

(b) 1,3-Dimethyl-7-(5,6-dihydroxyhexyl)xanthine

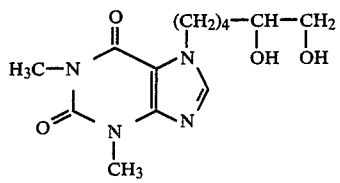

0.24 ml of perchloric acid (70% strength) was added dropwise with stirring in 5 minutes to a solution of 3.6 g of 1,3-dimethyl-7-(5,6-epoxyhexyl)xanthine in 280 ml of a mixture of ethylene glycol dimethyl ether and water (volume ratio 3:2) at room temperature. After stirring at room temperature for 16 hours, the mixture was neutralized with sodium bicarbonate solution and evaporated under reduced pressure. The residue was purified by column chromatography on silica gel (mobile phase: chloroform/ethanol, volume ratio 8/2) and recrystallization from ethyl acetate.

Yield:
3 g (78.3% of theory),
Melting point: 98°–100° C.,
$C_{13}H_{20}N_4O_4$ (MW=296.3).

Analysis: calculated: C 52.69%; H 6.80%; N 18.91%; found: C 52.39%; H 6.72%; N 18.83%.

Both the reaction of 1,3-dimethyl-7-(5-hexenyl)xanthine with osmium tetroxide in analogy to Example 2C) and also the alkylation of 1,3-dimethylxanthine with 1-chloro-5,6-isopropylidenedioxyhexane and subsequent acid hydrolysis of the dioxolane ring according to Example 1 or 2A) led to the same compound.

EXAMPLE 4

1,3-Dibutyl-7-(3,4-dihydroxybutyl)xanthine (a) 1,3-Dibutyl-7-(3,4-epoxybutyl)xanthine

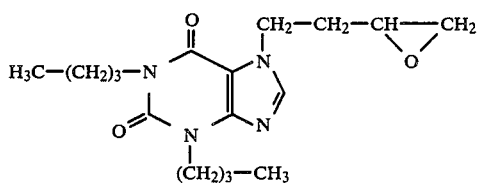

39.4 g of m-chloroperbenzoic acid (70% pure) were added to a solution of 42.7 g of 1,3-dibutyl-7-(3-butenyl)xanthine in 900 ml of chloroform within 15 minutes, with stirring. After stirring at room temperature for 27 hours, the mixture was washed with 10% strength sodium dithionite solution, saturated sodium bicarbonate solution and water, dried and evaporated under reduced pressure. The residue was chromatographed on a silica gel column with a mixture of methylene chloride/acetone (7:3, v:v) and recrystallized from petroleum ether.

Yield:
19 g (42.4% of theory),
Melting point: 52°-53° C.,
$C_{17}H_{26}N_4O_3$ (MW=334.4).

Analysis: calculated: C 61.06%; H 7.84%; N 16.75%; found: C 61.01%; H 7.89%; N 16.74%.

(b) 1,3-Dibutyl-7-(3,4-dihydroxybutyl)xanthine

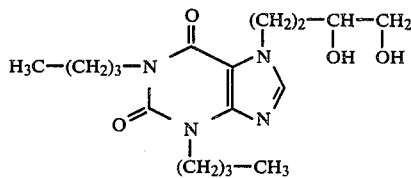

0.4 ml of perchloric acid (70% strength) was added dropwise with stirring in 5 minutes to a solution of 7 g of 1,3-dibutyl-7-(3,4-epoxybutyl)xanthine in 300 ml of a mixture of ethylene glycol dimethyl ether/water (volume ratio 3:2) at room temperature. After stirring at room temperature for 45 hours, the mixture was neutralized with sodium bicarbonate and the solution was evaporated. The residue was taken up with methylene chloride and purified by column chromatography on silica gel with a mixture of chloroform and ethanol (volume ratio 8:2) as the mobile phase and by recrystallization from methylene chloride/petroleum ether.

Yield:
4.8 g (65% of theory),
Melting point: 92°-93° C.,
$C_{17}H_{28}N_4O_4$ (MW=352.4).

Analysis: calculated: C 57.94%; H 8.00%; N 15.90%; found: C 58.06%; H 8.06%; N 15.77%.

Alternatively, this diol can be obtained by a one-step oxidation of 1,3-dibutyl-7-(3-butenyl)xanthine with osmium tetroxide in analogy to Example 2C) or by alkylation of 1,3-dibutylxanthine with the 1-halogeno-3,4-isopropylidenedioxybutanes known from the literature (for example Tetrahedron 34 (1978), pages 2,873–2,878) and subsequent acid hydrolysis of the dioxolane ring in analogy to Example 1.

EXAMPLE 5

1,3-Diethyl-7-(6,7-dihydroxyheptyl)xanthine (a) 1-Bromo-6,7-epoxyheptane

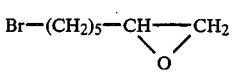

37.3 g of 1-bromo-6-heptene were added dropwise within 40 minutes, with stirring and flushing with nitrogen, to 50.9 g of m-chloroperbenzoic acid (85% pure) in 300 ml of methylene chloride at room temperature.

After standing overnight, the precipitate was filtered off with suction and the filtrate was washed with 10% strength $Na_2S_2O_4$ solution, with saturated sodium bicarbonate solution and with water and (after drying) evaporated under reduced pressure. 42.2 g of crude 1-bromo-6,7-epoxyheptane were obtained.

(b) 1-Bromo-6,7-dihydroxyheptane

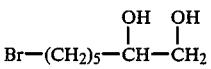

42 g of 1-bromo-6,7-epoxyheptane were introduced into a mixture of 400 ml of tetrahydrofuran and 235 ml of water, which had been adjusted to pH 2 with perchloric acid, at room temperature. After stirring at room temperature for 8 hours, the mixture was neutralized, evaporated under reduced pressure and the residue was extracted with methylene chloride. After removal of the solvent, 41.5 g of crude 1-bromo-6,7-dihydroxyheptane were obtained.

(c) 1-Bromo-6,7-isopropylidenedioxyheptane

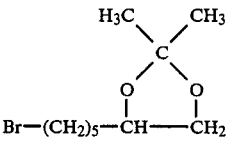

0.1 ml of concentrated sulfuric acid was added, with stirring under nitrogen, to 41 g of 1-bromo-6,7-dihydroxyheptane and 22.2 g of 2,2-dimethoxypropane in 100 ml of acetone at room temperature. After 4 hours, 0.6 g of sodium bicarbonate was added. After stirring for a further one hour, the solid was filtered off, the filtrate was evaporated under reduced pressure and the residue was subjected to fractional vacuum distillation.

Yield:
38 g (77.9% of theory),
Boiling point (0.4 mbar) 73°–76° C.,
Refractive index $n_D^{20} = 1.4656$.

(d) 1,3-Diethyl-7-(6,7-dihydroxyheptyl)xanthine

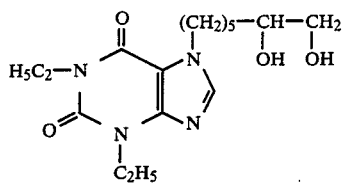

13.9 g of 1,3-diethylxanthine, 18 g of 1-bromo-6,7-isopropylidenedioxyheptane and 9.5 g of potassium carbonate in 100 ml of dimethylformamide were heated at 100° C. with stirring for 7 hours. After evaporation under reduced pressure, dilute sodium hydroxide solution was added to the residue and this was extracted several times with methylene chloride. The collected methylene chloride phases were washed with water, dried and evaporated. The residue was distilled in a bulbtube apparatus under 0.01 mbar and at a bath temperature of 100°-115° C. 17 g of 1,3-diethyl-7-(6,7-isopropylidenedioxyheptyl)xanthine were obtained, which were taken up in 70 ml of sulfuric acid at a pH of 0.5 and heated under reflux for 2 hours. After cooling, the mixture was neutralized, evaporated under reduced pressure and the residue was recrystallized from methylene chloride/diethyl ether.

Yield:
13.8 g (61.1% of theory),
Melting point 105° C.,
$C_{16}H_{26}N_4O_4$ (MW=338.4).
Analysis: calculated: C 56.79%; H 7.74%; N 16.56%; found: C 56.83%; H 7.70%; N 16.67%.

The 1-bromo-6,7-dihydroxyheptane prepared in step (b) can also be employed directly for the alkylation of the 1,3-diethylxanthine in step (d) without previous reaction with 2,2-dimethoxypropane to give the dioxolane derivative.

EXAMPLE 6

3,7-Diethyl-1-(4,5-dihydroxyhexyl)xanthine (a) 1-Chloro-4-hexene

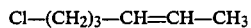

476 g (4 moles) of thionyl chloride were added from a dropping funnel to a solution of 330 g (3.3 moles) of 4-hexen-1-ol (Organic Syntheses, Vol. 55, page 62 et seq.) in 400 ml of pyridine, with stirring and cooling in ice, in such a manner that the reaction temperature did not exceed 55° C. The mixture was then heated at 80° C. for 1 hour. Thereafter, the mixture was allowed to cool down slowly, water was added and the mixture was extracted several times with diethyl ether. The combined other extracts were extracted by shaking with saturated sodium bicarbonate solution, washed with water to neutrality, dried over sodium sulfate and evaporated under normal pressure. 1-Chloro-4-hexene, which was pure by gas chromatography, was obtained by fractional distillation of the residue under reduced pressure.

Yield:
196.2 g (50.1% of theory),
Boiling point (140 mbar) 80° C.,
Refractive index $n_D^{21}=1.4400$.

(b) 3,7-Diethyl-1-(4,5-dihydroxyhexyl)xanthine

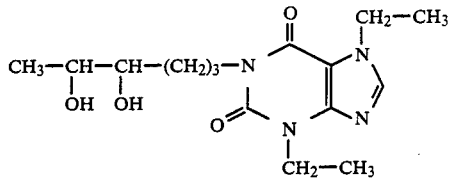

2.8 g (0.1 mole) of 3,7-diethylxanthine, 15.2 g (0.11 mole) of potassium carbonate and 13.0 g (0.11 mole) of 1-chloro-4-hexene in 600 ml of dimethylformamide were stirred at 110° C. for 18 hours. After cooling down, the mixture was filtered, the filtrate was evaporated under reduced pressure and the residue was taken up in chloroform. The unreacted 3,7-diethylxanthine was removed by extracting with 1N sodium hydroxide solution by shaking, the organic phase was washed to neutrality with water, dried over sodium sulfate and the solvent was distilled off in a rotary evaporator. After drying the solid residue from evaporation, 27.5 g (94.7% of theory) of crude 3,7-diethyl-1-(4-hexenyl)xanthine were obtained,

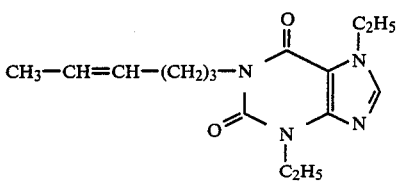

which, after dissolving in 350 ml of chloroform and adding 23.1 g (0.114 mole) of 3-chloroperbenzoic acid (85% pure), was stirred under a nitrogen atmosphere at room temperature for 48 hours. The mixture was then initially extracted by shaking with 10% strength sodium dithionite solution until the iodine-starch reaction disappeared, and then with 10% strength sodium bicarbonate solution, and the solution was washed with water until neutral and free of salt, dried and evaporated under reduced pressure. 29.0 g (100% of theory) of crude 3,7-diethyl-1-(4,5-epoxyhexyl)xanthine were obtained

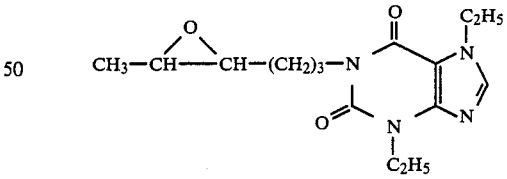

which, after being taken up in a solvent mixture composed of 150 ml of tetrahydrofuran and 100 ml of water and addition of 0.46 ml of perchloric acid (70% strength), was stirred at room temperature for 90 hours. The mixture was then neutralized with saturated sodium bicarbonate solution, the solvent was distilled off under reduced pressure and the residue was chromatographed on silica gel with chloroform as the mobile phase. This produced 26.4 g (86% of theory) of a crystalline product, which was recrystallized from ethyl acetate/petroleum ether, and which was almost pure by thin-layer chromatography.

Yield:

21.5 g (70% of theory),
Melting point 91°-93° C.,
C₁₅H₂₄N₄O₄ (MW=324.4).

Analysis: calculated: C 55.54%; H 7.46%; N 17.27%; found: C 55.54%; H 7.59%; N 16.97%.

The same compound was obtained by a one-step oxidation of 3,7-diethyl-1-(4-hexenyl)xanthine with osmium tetroxide in analogy to Example 2C).

EXAMPLE 7

3-Butyl-1-(4,5-dihydroxypentyl)-7-methylxanthine

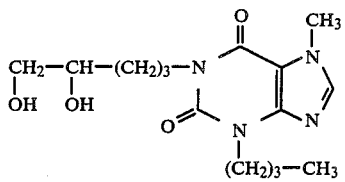

33.3 g (0.15 mole) of 3-butyl-7-methylxanthine, 24.3 g (0.16 mole) of 1-bromo-4-pentene and 22.1 g (0.16 mole) of potassium carbonate in 500 ml of dimethylformamide were heated with stirring at 100° C. for 15 hours. After cooling down, the reaction mixture was evaporated under reduced pressure, the residue was taken up in methylene chloride, filtered and the filtrate was extracted by shaking with 1N sodium hydroxide solution, the organic phase was washed with water to neutrality, dried over sodium sulfate and solvent was removed in a rotary evaporator. This produced 42.2 g (97% of theory) of crude, crystalline 3-butyl-7-methyl-1-(4-pentenyl)xanthine

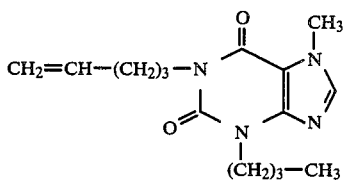

which was dissolved in 550 ml of chloroform, 35.6 g (0.175 mole) of 3-chloroperbenzoic acid (85% pure) were added and the mixture, after covering with an atmosphere of nitrogen, was stirred at room temperature for 67 hours. Extraction by shaking with 10% strength sodium dithionite solution until disappearance of the iodine-starch reaction, washing, initially with 10% strength sodium bicarbonate solution and then with water, drying over sodium sulfate and evaporation under reduced pressure provided 37.7 g (84.7% of theory) of crude 3-butyl-1-(4,5-epoxypentyl)-7-methylxanthine,

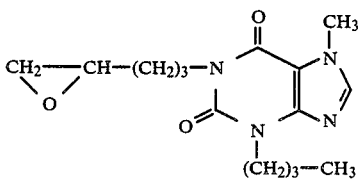

which was subjected to hydrolytic opening of the oxirane ring without intermediate purification. For this purpose, the 37.7 g of epoxide was dissolved in a mixture of 200 ml of tetrahydrofuran and 135 ml of water, and 0.61 ml of perchloric acid (70% strength) was added dropwise with stirring within about 10 minutes at room temperature. After stirring at room temperature for 14 hours, the mixture was neutralized with saturated sodium bicarbonate solution and evaporated under reduced pressure. The remaining oily crude product (100% of theory) could be purified by column chromatography on silica gel with chloroform/methanol (volume ratio 10/1) as the eluting agent and subsequent recrystallization from ethyl acetate with the addition of petroleum ether at the boiling point until cloudy.

Yield:
29.2 g (73.2% of theory),
Melting point 76°-78° C.,
C₁₅H₂₄N₄O₄ (MW=324.4).

Analysis: calculated: C 55.54%; H 7.46%; N 17.27%; found: C 55.38%; H 7.45%; N 17.62%.

The same compound was obtained by direct dihydroxylation of the C=C double bond of 3-butyl-7-methyl-1-(4-pentenyl)xanthine with osmium tetroxide in analogy to Example 2C).

EXAMPLE 8

1,7-Diethyl-3-(5,6-dihydroxyhexyl)xanthine (a) 1,7-Diethylxanthine

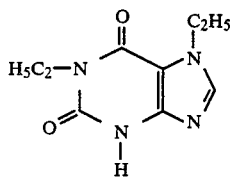

18 g of 3-benzyl-1,7-diethylxanthine (melting point 119° C.) in 1,500 ml of glacial acetic acid were hydrogenated in the presence of 2.5 g of 10% palladium on active charcoal at 80° C. and under 3.4 bar while shaking for 47 hours. After cooling down, the mixture was covered with an atmosphere of nitrogen while the catalyst was filtered off and the filtrate was evaporated under reduced pressure. The residue was dissolved in a mixture of 250 ml of methylene chloride and 100 ml of 1N sodium hydroxide solution. After washing the methylene chloride phase again with 1N sodium hydroxide solution, the combined aqueous phases were adjusted to pH 6 by adding 33% strength sulfuric acid dropwise with stirring. After washing to neutrality and drying the precipitate produced, 8.1 g (64.5% of theory) of 1,7-diethylxanthine, of melting point 204°-205° C., were obtained.

4.6 g of 3-benzyl-1,7-diethylxanthine were recovered from the methylene chloride phase.

(b) 1,7-Diethyl-3-(5,6-dihydroxyhexyl)xanthine

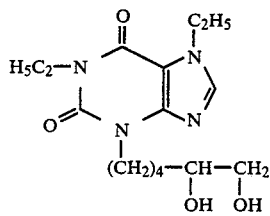

A mixture of 7 g of 1,7-diethylxanthine, 7.2 g of 1-chloro-5,6-isopropylidenedioxyhexane, 5 g of potassium carbonate and 50 ml of dimethylformamide was stirred at 120° C. for 8 hours. After evaporation under reduced pressure, the residue was taken up with 50 ml of 1N sodium hydroxide solution and extracted with methylene chloride. The methylene chloride phase was washed again with dilute sodium hydroxide solution, washed to neutrality, dried and evaporated under reduced pressure. The residue was distilled under 0.01 to 0.02 mbar and at a bath temperature of 120°-150° C. in a thin-layer evaporator and 11.5 g of 1,7-diethyl-3-(5,6-isopropylidenedioxyhexyl)xanthine were obtained. This was taken up with 325 ml of methanol and 80 ml of water and, after the addition of 0.4 ml of perchloric acid (70% strength), stirred at 70° C. for 1 hour. After cooling down to room temperature, the mixture was neutralized with sodium bicarbonate solution and evaporated to dryness under reduced pressure. The residue was taken up with 200 ml of methylene chloride and the extract was evaporated.

The residue was purified by column chromatography on silica gel with methylene chloride/ethanol (volume ratio 8/2) as the mobile phase and by subsequent recrystallization from methylene chloride/diethyl ether.

Yield:
7.9 g (72.5% of theory),
Melting point: 115°-116° C.,
$C_{15}H_{24}N_4O_4$ (MW=324.4).

Analysis: calculated: C 55.54%; H 7.46; N 17.27%; found: C 55.37%; H 7.51%; N 17.08%.

This diol was also obtained by reaction of 1,7-diethyl-3-(5-hexenyl)xanthine with osmium tetroxide in analogy to Example 2C) or by epoxidation of the foregoing xanthine compound, followed by acid hydrolysis of the epoxide ring in analogy to Examples 3, 4 and 7.

EXAMPLE 9

7-(2,3-Dihydroxybutyl)-1,3-dipropylxanthine (a) 1-Chloro-2,3-epoxybutane

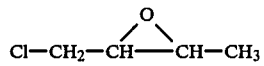

93.4 g of crotyl chloride (97% pure) were added dropwise with stirring within one hour to a solution of 244 g of 3-chloroperbenzoic acid (85% pure) in 1.5 l of chloroform while cooling in ice. After stirring for a further 70 hours at room temperature, the precipitate was filtered off with suction, and the filtrate was washed with 10% strength sodium dithionite solution (until the starch-iodine test was negative), with saturated sodium bicarbonate solution and with water. After drying over sodium sulfate, the solution was fractionally distilled over a packed column.

Yield:
58 g (54.3% of theory),
Boiling point (133 mbar) 70°-73° C.,
Refractive index $n_D^{20}=1.4327$,
$C_4H_7ClO$ (MW=106.55).

Analysis: calculated: C 45.09%; H 6.62%; Cl 33.27%; found: C 45.28%; H 6.78%; Cl 33.30%.

(b) 1-Chloro-2,3-dihydroxybutane

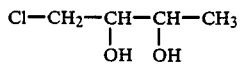

57 g of 1-chloro-2,3-epoxybutane were stirred in a mixture of 500 ml of water, 800 ml of tetrahydrofuran and 1.2 ml of perchloric acid (70% strength) at room temperature for 7 days. After neutralization with sodium bicarbonate solution, the mixture was evaporated to dryness under reduced pressure and the residue was taken up with 2 l of diethyl ether. The ethereal solution was dried and evaporated under reduced pressure.

Yield:
54 g (81% of theory).

1-Chloro-2,3-isopropylidenedioxybutane

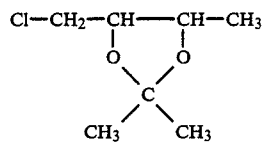

1 ml of perchloric acid (70% strength) was added dropwise with stirring within 6 minutes to a solution of 53 g of 1-chloro-2,3-dihydroxybutane in 50 ml of acetone and 71 g of 2,2-dimethoxypropane under an atmosphere of nitrogen at room temperature. After stirring at room temperature for a further hour, 5 g of finely powdered sodium bicarbonate was added, the mixture was stirred for half an hour, filtered and the filtrate was distilled over a packed column.

Yield:
36.8 g (52.5% of theory),
Boiling point (6.5 mbar) 49°-53° C.

(d) 7-(2,3-Dihydroxybutyl)-1,3-dipropylxanthine

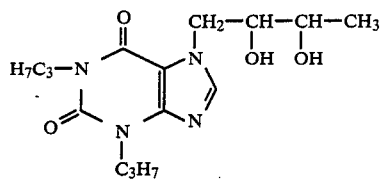

A mixture of 47.2 g of 1,3-dipropylxanthine, 33.6 g of 1-chloro-2,3-isopropylidenedioxybutane, 28.2 g of potassium carbonate and 300 ml of dimethylformamide was stirred at 120° C. for 8 hours. The mixture was evaporated under reduced pressure and the residue was taken up with 250 ml of 1N sodium hydroxide solution and 500 ml of methylene chloride. After washing the aqueous phase again with methylene chloride, the combined methylene chloride phases were washed with 1N sodium hydroxide solution and water, dried and evaporated under reduced pressure. The residue was distilled in a bulb-tube apparatus under 0.03-0.07 mbar and at a bath temperature of 90° C. 26.8 g of 7-(2,3-isopropylidenedioxybutyl)-1,3-dipropylxanthine (91.5% of theory relative to reacted 1,3-dipropylxanthine) were obtained,

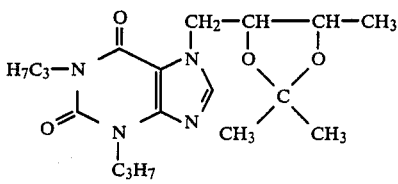

which was stirred in a mixture of 700 ml of tetrahydrofuran, 100 ml of water and 0.8 ml of perchloric acid (70% strength) at 70° C. for 1 hour. After neutralization with sodium bicarbonate solution, the mixture was evaporated under reduced pressure, the residue was taken up with 800 ml of methylene chloride, and the solution was dried and evaporated under reduced pressure. The residue was purified by recrystallization from methylene chloride/diethyl ether.

Yield:
20.9 g (87.6% of theory),
Melting point: 99°–101° C.,
$C_{15}H_{24}N_4O_4$ (MW=324.39).
Analysis: calculated: C 55.54%; H 7.46%; N 17.27%; found: C 55.49%; H 7.49%; N 17.18%.

The compounds aforementioned and those prepared in an analogous manner are compiled in Table 1.

TABLE 1

Compounds according to formula I

| Example | $R^1$ | $R^2$ | $R^3$ | Melting point, °C. or $n_D^{20}$ | Prepared in analogy to Example No. |
|---|---|---|---|---|---|
| 1 | $-C_3H_7$ | $-C_2H_5$ | $-(CH_2)_4-CH(OH)-CH_2OH$ | 96–98 | see description |
| 2 | $-C_2H_5$ | $-C_2H_5$ | $-(CH_2)_4-CH(OH)-CH_2OH$ | 94–95 | see description |
| 3 | $-CH_3$ | $-CH_3$ | $-(CH_2)_4-CH(OH)-CH_2OH$ | 98–100 | see description |
| 4 | $-C_4H_9$ | $-C_4H_9$ | $-(CH_2)_2-CH(OH)-CH_2OH$ | 92–93 | see description |
| 5 | $-C_2H_5$ | $-C_2H_5$ | $-(CH_2)_5-CH(OH)-CH_2OH$ | 105 | see description |
| 6 | $-(CH_2)_3-CH(OH)-CH(OH)-CH_3$ | $-C_2H_5$ | $-C_2H_5$ | 91–93 | see description |
| 7 | $-(CH_2)_3-CH(OH)-CH_2OH$ | $-C_4H_9$ | $-CH_3$ | 76–78 | see description |
| 8 | $-C_2H_5$ | $-(CH_2)_4-CH(OH)-CH_2OH$ | $-C_2H_5$ | 115–116 | see description |
| 9 | $-C_3H_7$ | $-C_3H_7$ | $-CH_2-CH(OH)-CH(OH)-CH_3$ | 99–101 | see description |
| 10 | $-(CH_2)_4-CH(OH)-CH_2OH$ | $-C_3H_7$ | $-CH_3$ | 112–113 | 2 (A) |
| 11 | $-C_{10}H_{21}$ | $-CH_3$ | $-(CH_2)_2-CH(OH)-CH_2OH$ | 107–108 | 3, 4 |
| 12 | $-C_3H_7$ | $-C_3H_7$ | $-(CH_2)_2-CH(OH)-CH_2OH$ | 93–95 | 3, 4 |
| 13 | $-C_3H_7$ | $-C_3H_7$ | $-(CH_2)_3-CH(OH)-CH_2OH$ | 83–84 | 3, 4 |
| 14 | $-C_2H_5$ | $-C_4H_9$ | $-(CH_2)_3-CH(OH)-CH_2OH$ | 79–80 | 3, 4 |
| 15 | $-C_3H_7$ | $-C_2H_5$ | $-(CH_2)_3-CH(OH)-CH_2OH$ | 82–84 | 3, 4 |
| 16 | $-C_2H_5$ | $-C_2H_5$ | $-(CH_2)_2-CH(OH)-CH_2OH$ | 132–134 | 3, 4 |
| 17 | $-C_2H_5$ | $-CH_3$ | $-(CH_2)_4-CH(OH)-CH_2OH$ | 111–113 | 1 |

TABLE 1-continued

Compounds according to formula I

| Example | $R^1$ | $R^2$ | $R^3$ | Melting point, °C. or $n_D^{20}$ | Prepared in analogy to Example No. |
|---|---|---|---|---|---|
| 18 | $-C_3H_7$ | $-CH_3$ | $-(CH_2)_4-CH(OH)-CH_2OH$ | 78–79 | 1 |
| 19 | $-C_4H_9$ | $-CH_3$ | $-(CH_2)_4-CH(OH)-CH_2OH$ | 81–83 | 1 |
| 20 | $-CH_2-CH(CH_3)_2$ | $-CH_3$ | $-(CH_2)_4-CH(OH)-CH_2OH$ | 62–64 | 1 |
| 21 | $-C_5H_{11}$ | $-CH_3$ | $-(CH_2)_4-CH(OH)-CH_2OH$ | 84–85 | 1 |
| 22 | $-(CH_2)_2-CH(CH_3)_2$ | $-CH_3$ | $-(CH_2)_4-CH(OH)-CH_2OH$ | 71–73 | 1 |
| 23 | $-CH(CH_3)_2$ | $-CH_3$ | $-(CH_2)_4-CH(OH)-CH_2OH$ | 83–85 | 1 |
| 24 | $-CH_3$ | $-C_2H_5$ | $-(CH_2)_4-CH(OH)-CH_2OH$ | 100–101 | 1 |
| 25 | $-CH(CH_3)_2$ | $-C_2H_5$ | $-(CH_2)_4-CH(OH)-CH_2OH$ | $n_D^{20} = 1.5443$ | 1 |
| 26 | $-C_4H_9$ | $-C_2H_5$ | $-(CH_2)_4-CH(OH)-CH_2OH$ | 78–82 | 1 |
| 27 | $-CH_2-CH(CH_3)_2$ | $-C_2H_5$ | $-(CH_2)_4-CH(OH)-CH_2OH$ | 80–81 | 1 |
| 28 | $-C_5H_{11}$ | $-C_2H_5$ | $-(CH_2)_4-CH(OH)-CH_2OH$ | 77–78 | 1 |
| 29 | $-(CH_2)_2-CH(CH_3)_2$ | $-C_2H_5$ | $-(CH_2)_4-CH(OH)-CH_2OH$ | 79 | 1 |
| 30 | $-CH_3$ | $-C_3H_7$ | $-(CH_2)_4-CH(OH)-CH_2OH$ | 82–84 | 1 |
| 31 | $-C_2H_5$ | $-C_3H_7$ | $-(CH_2)_4-CH(OH)-CH_2OH$ | 80–82 | 1 |
| 32 | $-C_3H_7$ | $-C_3H_7$ | $-(CH_2)_4-CH(OH)-CH_2OH$ | 78–80 | 2 (A) |
| 33 | $-C_3H_7$ | $-C_2H_5$ | $-(CH_2)_3-CH(OH)-CH(OH)-CH_3$ | 91–92 | 6, 1 |
| 34 | $-CH_3$ | $-C_3H_7$ | $-(CH_2)_3-CH(OH)-CH(OH)-CH_3$ | 149 | 6, 1 |

TABLE 1-continued

Compounds according to formula I

| Example | R$^1$ | R$^2$ | R$^3$ | Melting point, °C. or $n_D^{20}$ | Prepared in analogy to Example No. |
|---|---|---|---|---|---|
| 35 | —CH$_3$ | —(CH$_2$)$_4$—CH(OH)—CH$_2$OH | —CH$_3$ | 153–154 | 8 |
| 36 | —(CH$_2$)$_2$—CH(OH)—CH$_2$OH | —CH$_3$ | —C$_4$H$_9$ | 88–89 | 7 |
| 37 | —(CH$_2$)$_2$—CH(OH)—CH$_2$OH | —CH$_3$ | —C$_6$H$_{13}$ | 43–45 | 7 |
| 38 | —(CH$_2$)$_2$—CH(OH)—CH$_2$OH | —C$_2$H$_5$ | —C$_2$H$_5$ | 94–96 | 7 |
| 39 | —(CH$_2$)$_2$—CH(OH)—CH$_2$OH | —CH$_3$ | —C$_{12}$H$_{25}$ | 63–65 | 7 |
| 40 | —(CH$_2$)$_3$—CH(OH)—CH$_2$OH | —CH$_3$ | —C$_3$H$_7$ | 83–85 | 7 |
| 41 | —(CH$_2$)$_3$—CH(OH)—CH$_2$OH | —CH$_3$ | —C$_5$H$_{11}$ | 105–107 | 7 |
| 42 | —(CH$_2$)$_3$—CH(OH)—CH$_2$OH | —C$_2$H$_5$ | —C$_2$H$_5$ | 114–116 | 7 |
| 43 | —(CH$_2$)$_4$—CH(OH)—CH$_2$OH | —CH$_3$ | —C$_3$H$_7$ | 97–100 | 2 (A) |
| 44 | —(CH$_2$)$_4$—CH(OH)—CH$_2$OH | —CH$_3$ | —C$_4$H$_9$ | 80–81 | 2 (A) |
| 45 | —(CH$_2$)$_4$—CH(OH)—CH$_2$OH | —CH$_3$ | —C$_5$H$_{11}$ | 87–88 | 2 (A) |
| 46 | —(CH$_2$)$_4$—CH(OH)—CH$_2$OH | —CH$_3$ | —C$_6$H$_{13}$ | 54–56 | 2 (A) |
| 47 | —(CH$_2$)$_4$—CH(OH)—CH$_2$OH | —C$_2$H$_5$ | —C$_2$H$_5$ | 92–93 | 2 (A) |
| 48 | —(CH$_2$)$_4$—CH(OH)—CH$_2$OH | —C$_2$H$_5$ | —C$_3$H$_7$ | 107–108 | 2 (A) |
| 49 | —(CH$_2$)$_4$—CH(OH)—CH$_2$OH | —C$_2$H$_5$ | —C$_4$H$_9$ | 82–83 | 2 (A) |
| 50 | —(CH$_2$)$_3$—CH(OH)—CH(OH)—CH$_3$ | —CH$_3$ | —C$_3$H$_7$ | 107 | 6 |
| 51 | —C$_3$H$_7$ | —C$_2$H$_5$ | —(CH$_2$)$_5$—CH(OH)—CH$_2$OH | 102–103 | 1, 5 |

TABLE 2

Intermediate products having a structural element of the formula IV (arrangement of the radicals $R^1$, $R^2$ and $R^3$ as for formula I)

| Compound | $R^1$ | $R^2$ | $R^3$ | Melting point, °C |
|---|---|---|---|---|
| 1a | $-(CH_2)_3-CH\underset{O}{\overset{\diagdown\diagup}{-}}CH_2$ | $C_2H_5$ | $CH_3$ | 76–77 |
| 2a | " | $C_4H_9$ | $CH_3$ | (Example 7) |
| 3a | $-(CH_2)_3-CH\underset{O}{\overset{\diagdown\diagup}{-}}CH-CH_3$ | $C_2H_5$ | $C_2H_5$ | (Example 6b) |
| 4a | $-(CH_2)_4-CH\underset{O}{\overset{\diagdown\diagup}{-}}CH_2$ | $CH_3$ | $CH_3$ | 99–100 |
| 5a | " | | $C_2H_5$ | 80 |
| 6a | $CH_3$ | $CH_3$ | $-(CH_2)_4-CH\underset{O}{\overset{\diagdown\diagup}{-}}CH_2$ | 59–60 |
| 7a | $C_2H_5$ | $C_2H_5$ | $-(CH_2)_3-CH\underset{O}{\overset{\diagdown\diagup}{-}}CH_2$ | 58–59 |
| 8a | $C_2H_5$ | $C_2H_5$ | $-(CH_2)_4-CH\underset{O}{\overset{\diagdown\diagup}{-}}CH_2$ | 58–59 |
| 9a | $C_4H_9$ | $C_4H_9$ | $-(CH_2)_2-CH\underset{O}{\overset{\diagdown\diagup}{-}}CH_2$ | 52–53 |

TABLE 3

Intermediate products having a structural element of the formula IX ($R^6=CH_3$; $R^4$, $R^7$ and n: see table; arrangement of $R^1$, $R^2$ and $R^3$ as for formula I)

| Compound | $R^1$ | $R^2$ | $R^3$ | Bulb-tube distillation °C | mbar | Melting point °C |
|---|---|---|---|---|---|---|
| 1b | H | $CH_3$ | n=4, $R^4$=H, $R^7$=$CH_3$ | | | 187–188 |
| 2b | H | $C_2H_5$ | n=4, $R^4$=$R^7$=H | | | 146 |
| 3b | H | $C_2H_5$ | n=4, $R^4$=H, $R^7$=$CH_3$ | | | 123–124 |
| 4b | $CH_3$ | $C_2H_5$ | n=4, $R^4$=H, $R^7$=$CH_3$ | 150 | 0,02 | |
| 5b | $C_2H_5$ | $C_2H_5$ | n=4, $R^4$=H, $R^7$=$CH_3$ | 130–150 | 0,027* | |
| 6b | " | " | n=5, $R^4$=H, $R^7$=$CH_3$ | 100–115 | 0,01 | |
| 7b | " | $C_3H_7$ | n=4, $R^4$=H, $R^7$=$CH_3$ | 150–160 | 0,02 | |
| 8b | $C_3H_7$ | $C_2H_5$ | n=4, $R^4$=H, $R^7$=$CH_3$ | 135–140 | 0,01 | |
| 9b | " | " | n=5, $R^4$=H, $R^7$=$CH_3$ | 130 | 0,02 | |
| 10b | " | $C_3H_7$ | n=4, $R^4$=H, $R^7$=$CH_3$ | 140–150 | 0,05 | |
| 11b | " | " | n=1, $R^4$=$R^7$=$CH_3$ | 90 | 0,03–0,07 | |
| 12b | $C_4H_9$ | $C_2H_5$ | n=4, $R^4$=H, $R^7$=$CH_3$ | 120–130 | 0,03 | |
| 13b | $C_5H_{11}$ | $CH_3$ | n=4, $R^4$=H, $R^7$=$CH_3$ | 130–140 | 0,03 | |
| 14b | " | $C_2H_5$ | n=4, $R^4$=H, $R^7$=$CH_3$ | 130–140 | 0,02 | |
| 15b | $C_2H_5$ | n=4, $R^4$=H, $R^7$=$CH_3$ | $C_2H_5$ | 120–150 | 0,01–0,02* | |
| 16b | n=4, $R^4$=H, $R^7$=$CH_3$ | $C_2H_5$ | $C_3H_7$ | 140–150 | 0,2 | |
| 17b | n=4, $R^4$=H, $R^7$=$CH_3$ | $C_3H_7$ | $CH_3$ | 140 | 0,2 | |

*Thin-layer evaporator

EXAMPLE 52

Medicament formulation

For the production of 1,000 coated tablets, 100 g of 3-ethyl-7-(5,6-dihydroxyhexyl)-1-propylxanthine (compound according to Example 1), 20 g of lactose, 30 g of corn starch, 8.5 g of talc, 0.5 g of colloidal silicic acid and 1 g of magnesium stearate were mixed and compressed to form tablet cores weighing 160 mg, which were then treated with a coating mixture composed of 40 g of sucrose, 23.5 g of talc and very small amounts of wax, titanium dioxide and gum arabic added so that the final weight of each of the coated tablets was 225 mg.

EXAMPLE 53

Medicament formulation

For the production of 1,000 coated tablets, 111.8 g of 3-ethyl-7-(5,6-isopropylidenedioxyhexyl)-1-propylxanthine (from Example 1), 20 g of lactose, 30 g of corn starch, 8.5 g of talc, 0.5 g of colloidal silicic acid and 1 g of magnesium stearate were mixed and compressed to form tablet cores weighing 171.8 mg, which were then treated with a coating mixture composed of 40 g of sucrose, 23.5 g of talc and very small amounts of wax, titanium dioxide and gum arabic added so that the final weight of each of the coated tablets was 240 mg.

EXAMPLE 54

Medicament formulation

For the production of 1,000 coated tablets, 100 g of 1,3-diethyl-7-(5,6-epoxyhexyl)xanthine (from Example 2 B)), 20 g of lactose, 30 g of corn starch, 8.5 g of talc, 0.5 g of colloidal silicic acid and 1 g of magnesium stearate were mixed and compressed to form tablet cores weighing 160 mg, which were then treated with a coating mixture composed of 40 g of sucrose, 23.5 g of talc and very small amounts of wax, titanium dioxide and gum arabic added so that the final weight of each of the coated tablets was 225 mg.

PHARMACOLOGICAL TESTING AND RESULTS

1. Bronchospasmolytic activity

The compounds according to the invention were tested for bronchospasmolytic activity essentially using the experimental design described by H. Konzett and R. Rössler (Arch. exp. Path. u. Pharmak. 195 (1940) 75), comparing with the standard therapeutic agent, theophylline-ethylenediamine, and with the two known 2,3-dihydroxypropyl compounds diphylline [7-(2,3-dihydroxypropyl)-1,3-dimethylxanthine] and 7-(2,3-dihydroxypropyl)-1,3-dipropylxanthine. In this method, the inhibition of experimental bronchspasms—induced by intravenous administration of amines having spasmogenic activity, such as acetylcholine, histamine and serotonine—in guinea-pigs of both sexes under urethane anaesthesia (1.25 g/kg i.p.) is investigated.

The test substances were administered in aqueous solution either intravenously (i.v.) or intraduodenally (i.d.). The $ED_{50}$ values, which represent that dose in mg/kg at which the experimentally produced spasm is decreased by one half compared to that in untreated animals, were determined graphically from the dose-activity curves.

2. Acute toxicity

Determination of the $LD_{50}$ values was by the standard method of the mortality occurring within 7 days among NMRI mice after a single intravenous (i.v.), intraperitoneal (i.p.) or oral (p.o.) administration.

The results of these investigations, which demonstrate the superiority of the compounds according to the invention corresponding to formula I compared to the standard product theophylline-ethylenediamine and the two other comparison substances (particularly taking into account the more favorable ratio of $LD_{50}$ to $ED_{50}$), are compiled in the following Table 4.

TABLE 4

| Compound from Example | Mode of administration | Results of the pharmacological tests | | | Toxicity* $LD_{50}$ (mouse i.v., i.p. or p.o.) mg/kg | Therapeutic index $\frac{LD_{50}}{ED_{50}}$ |
|---|---|---|---|---|---|---|
| | | Bronchospasmolytic effect ($ED_{50}$ in mg/kg) compared to | | | | |
| | | acetyl-choline | histamine | serotonine | | |
| 1 | i.v. | 2.0 | 0.2 | 0.3 | i.v.: 254 | 305 |
| | i.d. | 6.3 | 25.0 | 15.0 | p.o.: 1450 | 94 |
| 2 | i.v. | 2.0 | 2.0 | 2.0 | i.v.: 325 | 163 |
| 7 | i.v. | 3.0 | 6.5 | — | i.v.: >200 | >42 |
| 8 | i.v. | 6.5 | 6.5 | 2.0 | i.v.: >300 | >60 |
| 10 | i.v. | 3.0 | 3.0 | 3.0 | i.v.: 250 | 83 |
| 12 | i.v. | 6.5 | 10.0 | 10.0 | i.p.: >600 | >68 |
| 13 | i.v. | 6.5 | 6.5 | — | i.p.: 900 | 138 |
| 17 | i.v. | 2.0 | 6.5 | 6.5 | i.v.: >300 | >60 |
| 18 | i.v. | 6.5 | 6.5 | 6.5 | i.v.: 300 | 46 |
| 19 | i.v. | 2.0 | 2.0 | 3.0 | i.v.: 147 | 63 |
| 21 | i.v. | 3.0 | 3.0 | 3.0 | i.v.: 155 | 52 |
| 22 | i.v. | 1.0 | 3.0 | 6.5 | i.v.: 167 | 48 |
| 24 | i.v. | 6.5 | 2.0 | 0.0 | i.v.: 300 | 49 |
| 25 | i.v. | 2.0 | 6.5 | 2.0 | i.v.: >400 | >114 |
| 26 | i.v. | 2.0 | 1.6 | 0.6 | i.v.: 205 | 146 |
| 28 | i.v. | 2.0 | 3.0 | 3.0 | i.v.: 200 | 75 |
| 30 | i.v. | 6.5 | 2.0 | — | i.v.: 250 | 59 |
| 33 | i.v. | 6.0 | 3.0 | 2.0 | i.v.: >200 | >55 |
| 51 | i.v. | 2.0 | 2.0 | — | i.v.: 300 | 150 |
| Theophylline-ethylenediamine | i.v. | 8.3 | 5.6 | 7.3 | i.v.: 195 | 28 |
| | i.d. | 40.0 | 50.0 | 50.0 | p.o.: 550 | 12 |
| Diphylline | i.v. | >30.0 | >30.0 | >30.0 | i.v.: 886(**) | >30 |
| 7-(2,3-dihydroxy- | i.v. | >10.0 | 6.5 | 10.0 | i.v.: 287(**) | >32 |

TABLE 4-continued

| | | Results of the pharmacological tests | | | | |
|---|---|---|---|---|---|---|
| Compound from Example | Mode of administration | Bronchospasmolytic effect (ED$_{50}$ in mg/kg) compared to | | | Toxicity* LD$_{50}$ (mouse i.v., i.p. or p.o.) mg/kg | Therapeutic index $\frac{LD_{50}}{ED_{50}}$ |
| | | acetyl-choline | histamine | serotonine | | |
| propyl)-1,5-dipro-nylxenihine | | | | | | |

(*)determined by the method of Litchfield and Wilcoxon (J. Pharmacol. exp. Ther. 96 (1949), 99)
(**)according to German Offenlegungsschrift 2,716,402

The unequivocal superiority of the compounds according to the invention, especially compared to the xanthine derivative which is most frequently employed for the therapy of obstructive respiratory tract diseases, theophylline-ethylenediamine (aminophylline), was also impressively confirmed in further specific experiments:

Since it is regarded as proven that, apart from the biogenic amines, acetylcholine, histamine and serotonine, listed in Table 4, bradykinin also plays an important part as a mediator substance in the provocation of asthma attacks, the inhibitory effect on the bronchospasm induced in guinea-pigs with bradykinin was investigated. In this test, for example, the compound from Example 1, on intravenous (i.v.) administration, was found to have an ED$_{50}$ of 1-3 mg/kg and, after intraduodenal (i.d.) administration, an ED$_{50}$ of 4.0-6.3 mg/kg and thus was about 3 times and about 6 times respectively more effective than theophylline-ethylenediamine, for which the corresponding total ED$_{50}$ values were found to be 3-10 mg/kg i.v. and 25-40 mg/kg i.d.

The compounds of the formula I also exert a strong inhibitory effect on the bronchospasm induced with ovalbumin (1 mg/kg i.v.) in the presensitized guinea-pig, which is hardly affected by the customary xanthine derivatives. Thus, for example, the ED$_{50}$ value for the compound of Example 1 is between 6 and 12 mg/kg i.v., whilst theophylline-ethylenediamine shows no effect in this design of experiment with doses up to 12 mg/kg.

The superior bronchospasmolytic activity of the xanthines according to formula I was finally demonstrated in the pulmonary function test on the anaesthetized dog using the inhibition of the bronchospastic reactions induced with aerosols of acetylcholine, histamine and ascaris extract.

Thus, for example, the compound in Example 1 already showed a significant inhibitory effect at 12 mg/kg i.v., whilst theophylline, in doses up to 20 mg/kg i.v., proved to have no effect.

As has already been mentioned in the introduction, the bronchospasmolytic effect of theophylline, which is clinically well established, is contrasted by the considerable disadvantage of a very narrow therapeutic range combined with serious side-effects, particularly in the cardiovascular system (hypotensive activity, decrease in cerebral blood flow) and in the central nervous system (for example restlessness, insomnia and vertigo). The stimulation of the central nervous system is regarded by patients and clinicians as being particularly disturbing, since it frequently leads to insomnia and thus has a persistent adverse effect on the general state of health of the asthmatic patient. An expression of this stimulation of the central nervous system is the increase in spontaneous motility of male white mice by 186% over a period of 7 hours after oral administration of 30 mg/kg of theophylline-ethylenediamine. According to German Offenlegungsschrift 2,716,402, the other two comparison products diphylline and 7-(2,3-dihydroxypropyl)-1,3-dipropylxanthine also bring about a stimulation of the central nervous system in mice, although these effects are markedly less pronounced than for theophylline. In contrast, the compounds of the formula I according to the invention have no component stimulating the central nervous system, but, on the contrary, exert a slight depressant effect on the central nervous system which is assessed to be particularly advantageous from the therapeutic point of view. Thus, the spontaneous motility of mice, for example, is decreased by 53% for a period of 11 hours after oral administration of 50 mg/kg of the compound from Example 1.

The investigations of the circulatory system carried out on rats and dogs, comparing with theophylline-ethylenediamine, have shown that the compounds of the formula I have a hypotensive activity, if any at all, which is markedly lower and that they cause no decrease in cerebral blood flow.

We claim:

1. A compound of the formula

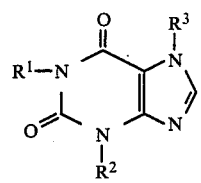

in which one of the radicals $R^1$, $R^2$ and $R^3$ represents a group of formula IV

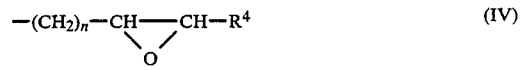

(IV)

or formula IX

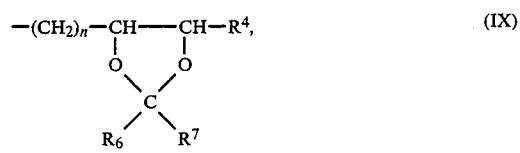

(IX)

$R^4$ denoting hydrogen or methyl; $R^6$ and $R^7$, independently of one another, being hydrogen, lower alkyl, phenylalkyl having up to 2 C atoms in the alkyl moiety or phenyl; n, when $R^4$ is hydrogen, denoting an integer from 2 to 6 and, when $R^4$ is methyl, denoting 1 to 5, the rest of the radicals $R^1$, $R^2$ and $R^3$, independently of one another, denoting hydrogen or alkyl having 1 to 12 C atoms in the positions $R^1$ and $R^3$ and having 1 to 4 C atoms in the position $R^2$, the total number of carbon atoms in these two radicals being a maximum of 14.

2. A compound as claimed in claim 1, wherein $R^1$ is hydrogen, alkyl having 1 to 5 C atoms or a radical of formula IX; and $R^2$ and $R^3$, independently of one another, are alkyl having 1 to 3 C atoms or a radical of formula IX.

3. A compound as claimed in claim 1 wherein $R^1$ represents a group of formula IV.

4. A compound as claimed in claim 1 wherein $R^2$ represents a group of formula IV.

5. A compound as claimed in claim 1 wherein $R^3$ represents a group of formula IV.

6. A compound as claimed in claim 1 wherein $R^1$ represents a group of formula IX.

7. A compound as claimed in claim 1 wherein $R^2$ represents a group of formula IX.

8. A compound as claimed in claim 1 wherein $R^3$ represents a group of formula IX.

9. A compound as claimed in claim 1 in which one of the radicals $R^1$, $R^2$, and $R^3$ represents a group of formula IX.

10. A compound of the formula

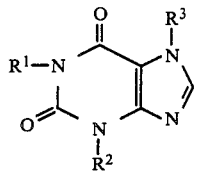

in which one of the radicals $R^1$, $R^2$ and $R^3$ represents a group of formula IV

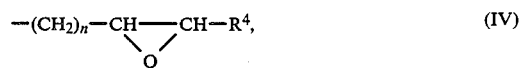

$R^4$ denoting hydrogen or methyl; n, when $R^4$ is hydrogen, denoting an integer from 2 to 6 and, when $R^4$ is methyl, denoting an integer from 1 to 5, and the radicals $R^1$, $R^2$ and $R^3$, independently of one another, denoting hydrogen or alkyl having 1 to 12 C atoms in the positions $R^1$ and $R^3$ and having 1 to 4 C atoms in the position $R^2$, the total number of carbon atoms in these two radicals being a maximum of 14.

11. A compound as claimed in claim 10, wherein $R^1$ or $R^3$ is the radical of formula IV and the other radicals, independently of one another, are alkyl having 1 to 4 C atoms.

* * * * *